United States Patent
Johnson et al.

(10) Patent No.: US 10,406,295 B2
(45) Date of Patent: Sep. 10, 2019

(54) RETAINER FOR RETRACTABLE NEEDLE ASSEMBLIES AND SYRINGES

(71) Applicant: UNL Holdings LLC, New York, NY (US)

(72) Inventors: Jeffrey M. Johnson, San Diego, CA (US); Kevin Bokelman, San Diego, CA (US); Jyoti Gupta, Atlanta, GA (US); Brandon J. McKee, Nesquehoning, PA (US)

(73) Assignee: UNL Holdings LLC, New York, NY (US)

( * ) Notice: Subject to any disclaimer, the term of this patent is extended or adjusted under 35 U.S.C. 154(b) by 746 days.

(21) Appl. No.: 14/907,964

(22) PCT Filed: Aug. 7, 2014

(86) PCT No.: PCT/US2014/050066
§ 371 (c)(1),
(2) Date: Jan. 27, 2016

(87) PCT Pub. No.: WO2015/021236
PCT Pub. Date: Feb. 12, 2015

(65) Prior Publication Data
US 2016/0175540 A1     Jun. 23, 2016

Related U.S. Application Data

(60) Provisional application No. 61/863,113, filed on Aug. 7, 2013.

(51) Int. Cl.
*A61M 5/32* (2006.01)
*A61M 5/178* (2006.01)
*A61M 5/31* (2006.01)

(52) U.S. Cl.
CPC ........ *A61M 5/3221* (2013.01); *A61M 5/3234* (2013.01); *A61M 5/1782* (2013.01);
(Continued)

(58) Field of Classification Search
CPC .............. A61M 5/3221; A61M 5/3234; A61M 5/1782; A61M 2005/3106;
(Continued)

(56) References Cited

U.S. PATENT DOCUMENTS

| | | |
|---|---|---|
| 4,874,382 A | 10/1989 | Lindemann et al. |
| 5,407,431 A | 4/1995 | Botich et al. |
| 6,096,005 A | 8/2000 | Botich et al. |

FOREIGN PATENT DOCUMENTS

| | | |
|---|---|---|
| CN | 2678666 Y | 2/2005 |
| CN | 101203256 A | 6/2008 |

(Continued)

OTHER PUBLICATIONS

European Patent Office, International Search Report and Written Opinion from International Application No. PCT/US2014/050066, 21 pgs (Mar. 31, 2015).

*Primary Examiner* — Manuel A Mendez
(74) *Attorney, Agent, or Firm* — Hamilton, Brook, Smith & Reynolds, P.C.

(57) ABSTRACT

A retainer for a needle assembly of a retractable syringe that includes a plunger assembly and a barrel having a mounting member. The needle assembly includes a retractable needle, a needle hub, and a retainer. The retractable needle is engageable by the plunger assembly to facilitate retraction thereof. The needle hub is mountable to the mounting member of the barrel. The retainer includes a body and at least one retaining member that extends distally from the body. The retaining member includes an inwardly projecting lateral projection to engage the retractable needle and thereby prevent inadvertent proximal movement of said retractable needle prior to retraction. A retractable needle (Continued)

assembly includes the retainer, and a retractable syringe includes the retractable needle assembly including the retainer. A syringe kit includes a retractable syringe, a plurality of retractable needle assemblies, and a vial adapter.

20 Claims, 15 Drawing Sheets

(52) U.S. Cl.
CPC ............... *A61M 2005/3106* (2013.01); *A61M 2005/3142* (2013.01); *A61M 2005/323* (2013.01); *A61M 2005/3231* (2013.01); *A61M 2005/3241* (2013.01)

(58) Field of Classification Search
CPC .... A61M 2005/3142; A61M 2005/323; A61M 2005/3231; A61M 2005/3241
USPC ......................................................... 604/198
See application file for complete search history.

(56) References Cited

FOREIGN PATENT DOCUMENTS

| | | |
|---|---|---|
| CN | 102695533 A | 9/2012 |
| CN | 102725014 A | 10/2012 |
| CN | 102791312 A | 11/2012 |
| WO | 2006108243 A2 | 10/2006 |
| WO | WO 2006-108243 A2 | 10/2006 |
| WO | WO 2011-057334 A1 | 5/2011 |
| WO | WO 2011-057335 A1 | 5/2011 |
| WO | WO 2011-075760 A1 | 6/2011 |

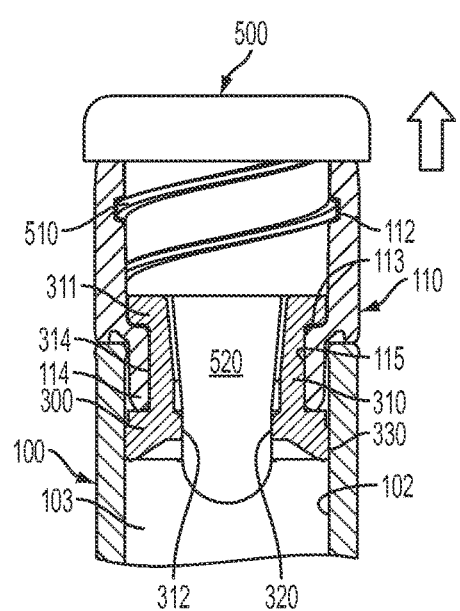
FIG. 9A
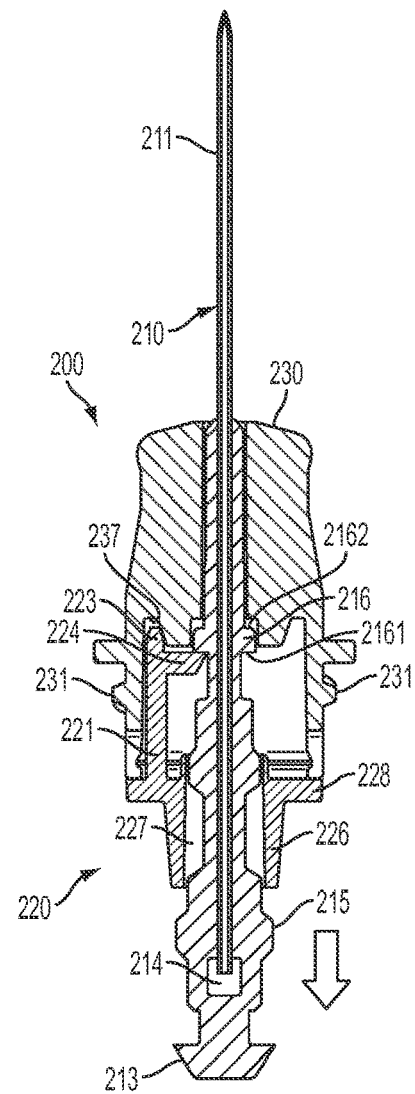
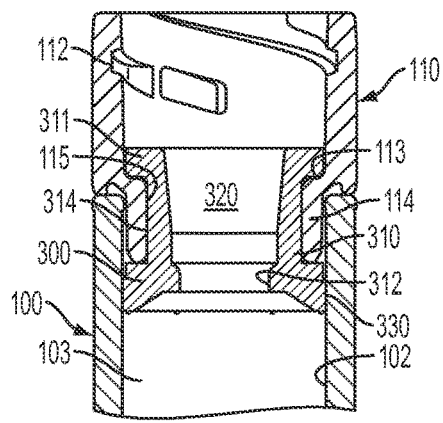
FIG. 9B

RETAINER FOR RETRACTABLE NEEDLE ASSEMBLIES AND SYRINGES

CROSS-REFERENCE TO RELATED APPLICATIONS

This application is a national phase application of International Patent Application No. PCT/US2014/050066, filed Aug. 7, 2014, published as WO2015/021236, which claims priority to U.S. Provisional Application No. 61/863,113, filed Aug. 7, 2013, both of which are incorporated by reference herein in their entireties for all purposes.

TECHNICAL FIELD

THIS INVENTION relates to syringes. More particularly, this invention relates to a retainer for a replaceable, retractable needle of a retractable syringe.

BACKGROUND OF THE INVENTION

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers. Further problems arise for health professionals administering medicines and vaccines to infected individuals, where accidental needle stick injury by a used syringe can lead to infection.

In response to this problem, syringes have been developed which either provide a needle sheathing mechanism or a needle retraction mechanism to prevent re-use and/or needle stick injury. However, many such retractable syringes have highly specialized retractable needle assemblies that are not amenable to replacing needles which have been bent or burred or for allowing a user to select an appropriate needle size. An additional complication is that it is difficult to ensure that retractable needles do not inadvertently move proximally (i.e., retract) into the barrel such as when piercing the skin prior to injection, while not resisting retraction after completion of injection. Retaining systems that achieve this balancing act can be difficult to design, particularly where the sometimes competing interests of costs of manufacture and reliability have to both be satisfied in a commercially-viable retractable syringe. These problems can be even more marked in the context of a retractable syringe having a replaceable, retractable needle assembly.

BRIEF SUMMARY OF THE INVENTION

The invention is therefore, at least in part, broadly directed to an improved retainer for a needle assembly for a retractable syringe. More particularly, the retainer is suitable for a replaceable, retractable needle assembly.

The invention also broadly relates to an improved needle retention and/or retraction mechanism comprising respective elements of the retractable needle assembly and/or a plunger capable of engaging and retracting a retractable needle.

In a first aspect, the invention provides a retainer for a needle assembly of a retractable syringe that includes a plunger assembly and a barrel having a mounting member. The needle assembly includes a retractable needle, a needle hub, and a retainer. The retractable needle is engageable by the plunger assembly to facilitate retraction thereof. The needle hub is mountable to the mounting member of the barrel. The retainer includes a body and at least one retaining member that extends distally from the body to engage the retractable needle and thereby prevent inadvertent proximal movement of the retractable needle.

In a second aspect, the invention provides a needle assembly for a retractable syringe that includes a plunger and a barrel having a mounting member. The needle assembly includes a needle that is engageable by the plunger, a needle hub that is mountable to the mounting member of the barrel, and a retainer. The retainer includes a body and one or more retaining members that extend or project distally from the body to engage the retractable needle and thereby prevent inadvertent proximal movement of the retractable needle.

In a third aspect, the invention provides a retractable syringe including a needle assembly, a plunger and a barrel having a mounting member. The needle assembly includes a retractable needle that is engageable by the plunger, a needle hub that is mountable to the mounting member of the barrel, and a retainer. The retainer includes a body and one or more retaining members that project distally from the body to engage the retractable needle and thereby prevent inadvertent proximal movement of the retractable needle.

In an embodiment, the retainer may include a body having a circumferential shoulder from which projects or extends one or more retaining members. Each retaining member may include at least one prong that includes at least one tip and at least one lateral projection. The at least one tip and/or at least one lateral projection may facilitate engagement with one or more other components of the needle assembly and/or a needle seal, as will be described in more detail hereinafter.

In an embodiment, the needle assembly is a retractable needle assembly. According to this embodiment, the needle assembly (and needle hub) is removably mountable to the mounting member. Typically, the mounting member and the needle hub include complementary mating members.

In one embodiment, the mounting member further includes a male fitment which is receivable by a female fitment of the needle hub (or vice versa). Preferably, the mounting member includes a screw-thread which in use is receivable by a complementary screw thread of the needle hub (or vice versa). In a particular embodiment, the mounting member may utilize a screw-thread and a male fitment to be received by a corresponding screw-thread and female fitment of the needle hub. This configuration may be similar to that known as a luer connection or, more specifically, a luer lock connection.

Preferably, the barrel includes a releasing member.

In one embodiment, the barrel further includes a collar.

Preferably, the collar includes the releasing member.

Suitably, the retractable syringe further includes a needle seal. Typically, the needle seal is mounted or located at least partly within the barrel and/or the mounting member. Suitably, the body of the retainer includes a portion that is capable of engaging a needle seal. Accordingly, the needle seal may be a component of the needle assembly, in at least one embodiment, for mounting to a barrel.

In one embodiment, the plunger includes: a biasing element; a plunger member releasably connected to a control rod; a plunger housing; and a plunger seal mounted to the plunger member; wherein the plunger member, control rod and plunger housing co-operate to maintain the biasing element in an initially energized state prior to retraction.

Suitably, the plunger includes a needle-engaging portion that is capable of engaging the retractable needle to facilitate retraction of the retractable needle.

Preferably, the plunger is arranged so that at the end of depression of the plunger to deliver fluid contents of the retractable syringe, the control rod disengages from the plunger housing to facilitate a release of energy from the biasing element to thereby retract the control rod and the plunger member with the retractable needle coupled thereto.

Suitably, the biasing member is any device which can store energy in a releasable form, such as a spring (e.g., a coil spring, leaf spring etc.) elastic or the like.

Preferably, the biasing element is a spring.

The retractable syringe may further include one or more locking systems to minimize or prevent re-use of the retractable syringe. In one embodiment, the plunger housing includes one or more lock elements capable of forming a locking system with the barrel, or a collar mounted to the barrel, at the end of retraction.

In a fourth aspect, the invention provides a retractable syringe kit including a barrel, a plunger and a plurality of retractable needle assemblies according to the second aspect.

In one embodiment of the retractable syringe kit, the plurality of needle assemblies include a 0.5 inch needle, a 1.0 inch needle, and a 1.5 inch needle, though a range of needle lengths and gauges may be utilized and incorporated within the needle assemblies and kits of the present invention.

In a particular embodiment, the retractable syringe kit further includes a vial adapter. In one particular form, the vial adapter includes a housing having a base, an adapter cannula that extends or projects from the base and a connector that is capable of being in fluid communication with fluid contents of a vial and the barrel of the retractable syringe, the adapter housing further including a shroud to protect a user from inadvertent needle-stick injury by the adapter cannula, the shroud including one or more arms that engage a vial closure. The shroud may further include one or more flexion arms that allow the vial adapter to engage any of a variety of different-sized vial closures. In use, the vial adapter facilitates transfer or delivery of fluid between the vial and the retractable syringe barrel to thereby allow fluid reconstitution of a powdered, dried, desiccated or dehydrated solid substance contained within the syringe barrel or within the vial. The vial adapter may further includes a conduit tip mountable or mounted to the connector in fluid communication with the adapter cannula, which conduit tip prevents inadvertent activation of the syringe retraction mechanism during fluid transfer.

Preferably, the vial adapter further includes a conduit tip mountable or mounted to the connector in fluid communication with the adapter cannula. In use, the conduit tip prevents inadvertent activation of the syringe retraction mechanism during fluid transfer.

In a fifth aspect, the invention provides a method of assembling a retractable syringe including the step of removably mounting the retractable needle assembly of the second aspect to a barrel of a retractable syringe.

Preferably, the method includes the step of removing a plug from a mounting member of the barrel prior to removably mounting the retractable needle assembly to the barrel.

In one embodiment, the method includes the step of screw-threadedly mounting a needle hub of the retractable needle assembly to a mounting member of the barrel.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE SEVERAL VIEWS OF THE DRAWING(S)

Non-limiting embodiments are described herein with reference to the following drawings wherein:

FIG. 9A is a fragmentary, partial cross-sectional view of an embodiment of a barrel to which is mounted a plug according to teachings of this disclosure.

FIG. 9B is a cross-sectional view of an embodiment of a retractable needle assembly prior to mounting in a barrel, the barrel being shown in as a fragmentary cross-sectional view.

DETAILED DESCRIPTION OF THE INVENTION

Figure 1:
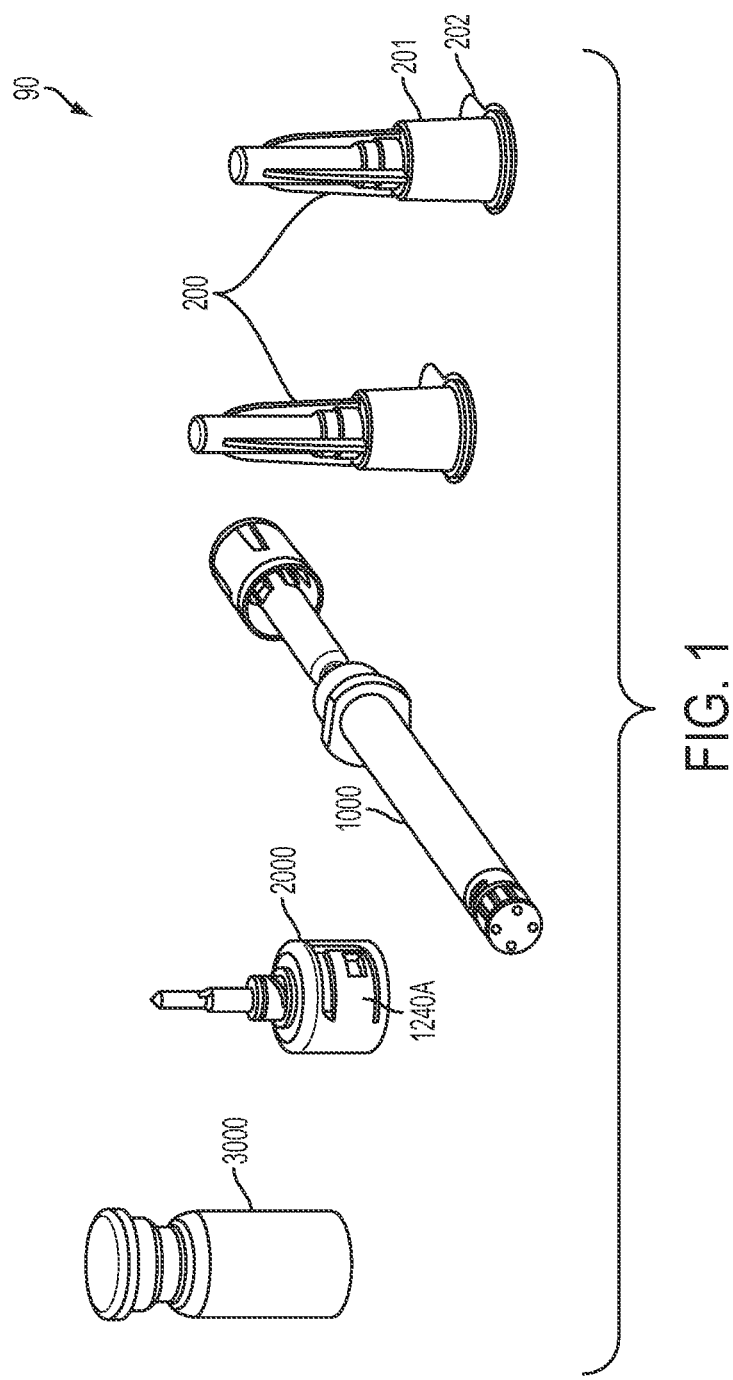
FIG. 1 is an isometric view of a retractable needle syringe kit according to teachings of this disclosure.
Figure 2:
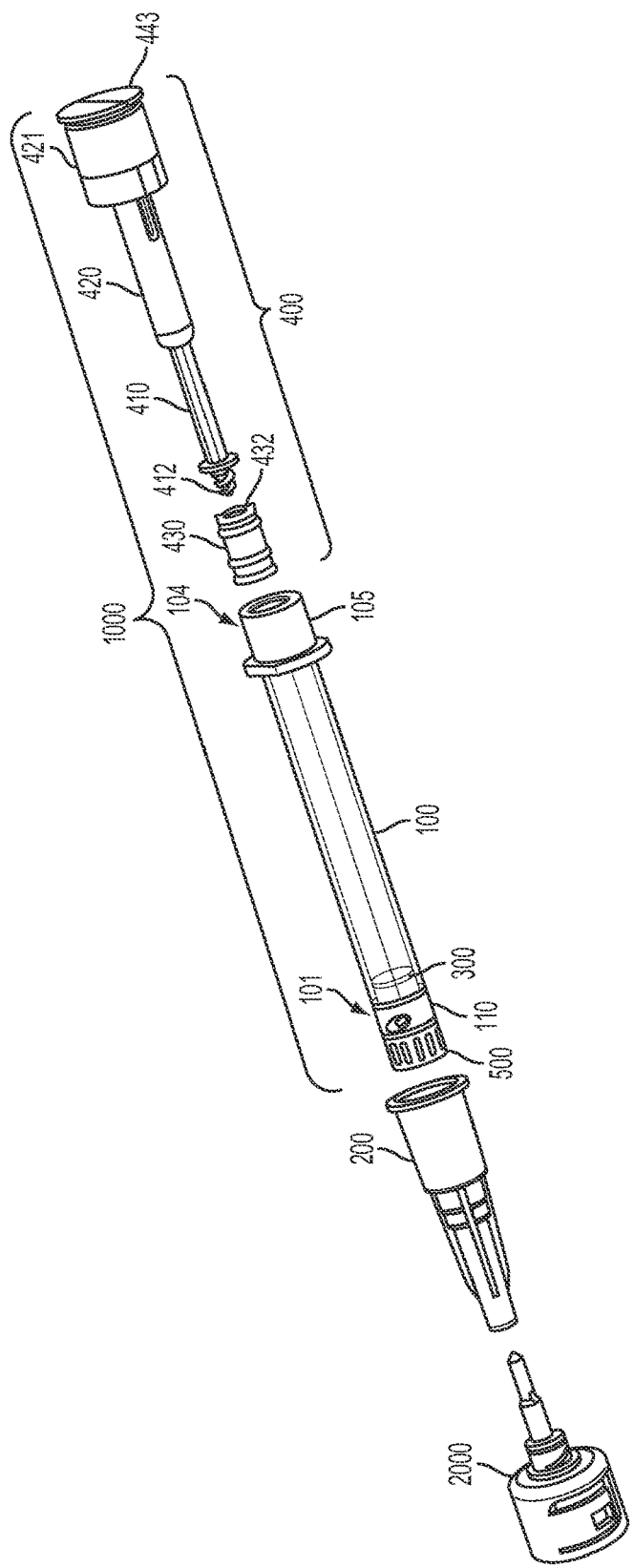
FIG. 2 is an exploded isometric view of the syringe and vial adapter of the kit of FIG. 1.

Referring to FIGS. 1 and 2, there is illustrated a syringe kit 90, which includes a syringe 1000, a selection of retractable needle assemblies 200, and a vial adapter 2000. The retractable needle assemblies 200 are contained within respective needle caps 201, which are then sealed with an appropriate cover 202 in order to maintain the sterile nature of the retractable needle assemblies 200. The cover 202 may be of any appropriate design, such as, for example, a removable film. Those of skill in the art will understand that a similar cap and cover arrangement or other structure may be provided to ensure the sterility of the vial adapter 2000.

Also illustrated in FIG. 1 is a vial 3000. Should the syringe 1000 contain a medicament that requires reconstitution or mixing with another component contained in such a vial 3000, the vial adapter 2000 may be utilized with the syringe 1000 and the vial 3000, as will be explained in greater detail below. Following reconstitution or mixing, the vial adapter 2000 and vial 3000 may be separated from the syringe 1000, and a retractable needle assembly 200 having a desired needle size may be attached to the syringe 1000 for administration to a patient.

Figure 3:
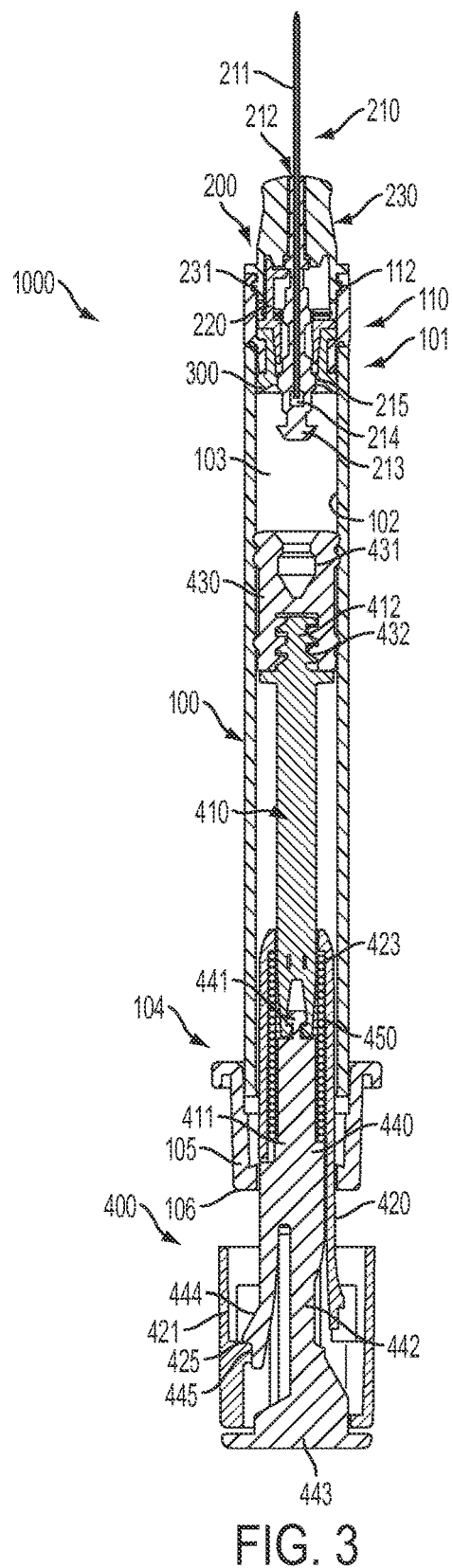
FIG. 3 is a cross-sectional view of an embodiment of a retractable syringe according to teachings of this disclosure.
Figure 4:
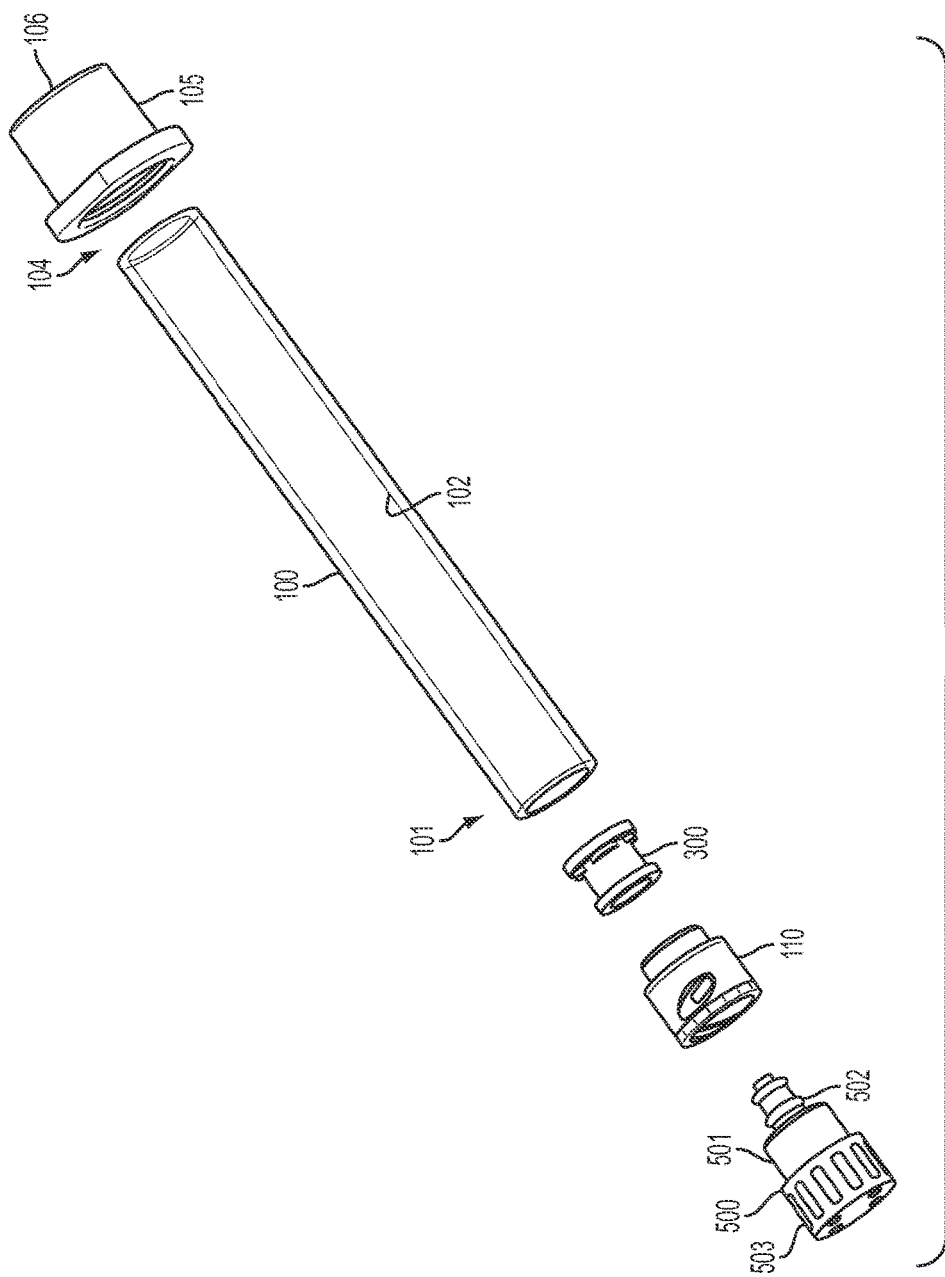
FIG. 4 is an exploded isometric view of a barrel assembly of a syringe according to teachings of this disclosure.

An embodiment of syringe 1000 according to teachings of the invention is illustrated in FIGS. 2-4. The syringe 1000 includes a barrel 100 with a mounting member 110 to which a retractable needle assembly 200 may be coupled, a needle seal 300 and a plunger assembly 400, which is slidably, axially moveable within barrel 100. For the purposes of this disclosure, the term "distal" will refer to the direction or end of the syringe 1000 and the components of the syringe toward the retractable needle assembly 200. Conversely, for the purposes of this disclosure, the term "proximal" will refer to the direction or end of the syringe 1000 and the components of the syringe toward the end of the barrel 100 which receives the plunger assembly 400.

Referring to FIG. 4, the barrel 100 is an elongated tubular structure having an internal wall 102. A collar 105 is disposed at the proximal end 104 of barrel 100. The collar 105 includes a releasing member 106, the significance of which will be explained below. The mounting member 110 is disposed at the distal end 101 of the barrel 100. The mounting member 110 is typically glued or otherwise firmly affixed to the barrel 100.

The needle seal 300 is disposed within at least one of the mounting member 110 and the internal wall 102 of the barrel 100. As may be seen more clearly in the enlarged views of FIGS. 9A-10B, the needle seal 300 includes a body 310 having a retaining rim 311, a needle aperture 320 and a peripheral sealing rim 330 that sealingly bears against the internal wall 102 of barrel 100. The retaining rim 311 engages a seat 113 along a recessed element 114 of the mounting member 110. The needle seal 300 may additionally be provided with a peripheral engagement surface 314 that engages a proximal surface 115 of the recessed element 114 of the mounting member 110. The needle seal 300 additionally includes an inner sealing rib 312, which projects into the needle aperture 320 of the needle seal 300 to seal against a peripheral sealing surface 215 of needle body 212 in assembly.

The internal wall 102 along with the needle seal 300 defines a fluid chamber 103 within the barrel 100. As shown in FIGS. 2 and 4, a mounting member cap or plug 500 that engages and closes the mounting member 110 may be provided in order to seal and maintain the sterility of the fluid chamber 103 within the barrel 100 when the plunger assembly 400 is disposed within the barrel 100 as described below. The mounting member cap or plug 500 is removably coupled to the mounting member 110, and includes sealing structure for maintenance of the contents and/or the sterility of the fluid chamber 103. In the embodiment illustrated in FIG. 4, the mounting member cap or plug 500 includes portion 501 that is disposed within the interior of the mounting member 110, one or more sealing rings 502 that are disposed within the needle aperture 320 and seal against the needle seal 300, and a protruding portion 503 that may be grasped by a user to remove the mounting member cap or plug 500 from the mounting member 110. In use, the mounting member cap or plug 500 is removed in order to couple the removable needle assembly 200 to the mounting member 110, or to engage the vial adapter 2000, as explained in greater detail below.

Returning again to FIG. 3, the plunger assembly 400 includes a plunger rod 410, a plunger housing 420, a control rod 440 and a plunger seal 430 coupled to plunger rod 410. The plunger seal 430 may be of any appropriate material, and is slidably and sealingly disposed within the barrel 100 in an assembled syringe 1000. The plunger rod 410 and plunger seal 430 typically include complementary engaging structures. For example, in the illustrated embodiment, the plunger rod 410 includes a "male" seal connector 412 that screw-threadedly engages complementary "female" plunger connector 432 of a plunger seal 430. Those of skill will appreciate that this orientation may be reversed. Indeed, other types of connections (i.e., other than screw-threaded) may be used. It is also contemplated that plunger seal 430 could be integrally formed with plunger rod 410.

The plunger housing 420 is generally cylindrical with a skirt 421 at its proximal end. The plunger housing 420 also includes an internal tab 425, here, at its proximal end and internal to the skirt 421.

The control rod 440 and the plunger rod 410 are at least partially disposed within the plunger housing 420. The control rod 440 includes a cantilevered arm 444 and a shaft 442, which supports an actuation button 443 operable by a user.

The control rod 440 is releasably coupled at its distal end to the plunger rod 410 by way of a releasable connection 441. In order to facilitate a retracting operation following administration of medication within the syringe 1000, the releasable connection 441 of plunger rod 410 and the control rod 440 disposes biasing element 450 in an energized position. In this embodiment, the biasing element 450 is spring. Accordingly, for the purposes of this disclosure, the terms "biasing element" and "spring" will both be utilized in conjunction with the reference numeral 450. Before retraction, a ridge 445 on the arm 444 of control rod 440 releasably engages the internal tab 425 inside the skirt 421 of the plunger housing 420 to retain the spring 450 in an initially compressed state. In this way, the spring 450 is compressed between an inner shoulder 423 of plunger housing 420 and annular ledge 411 of plunger control rod 440. In this context, "initially compressed" means that spring 450 is in a compressed (i.e., energized) state before use of retractable syringe 1000.

Figure 5:
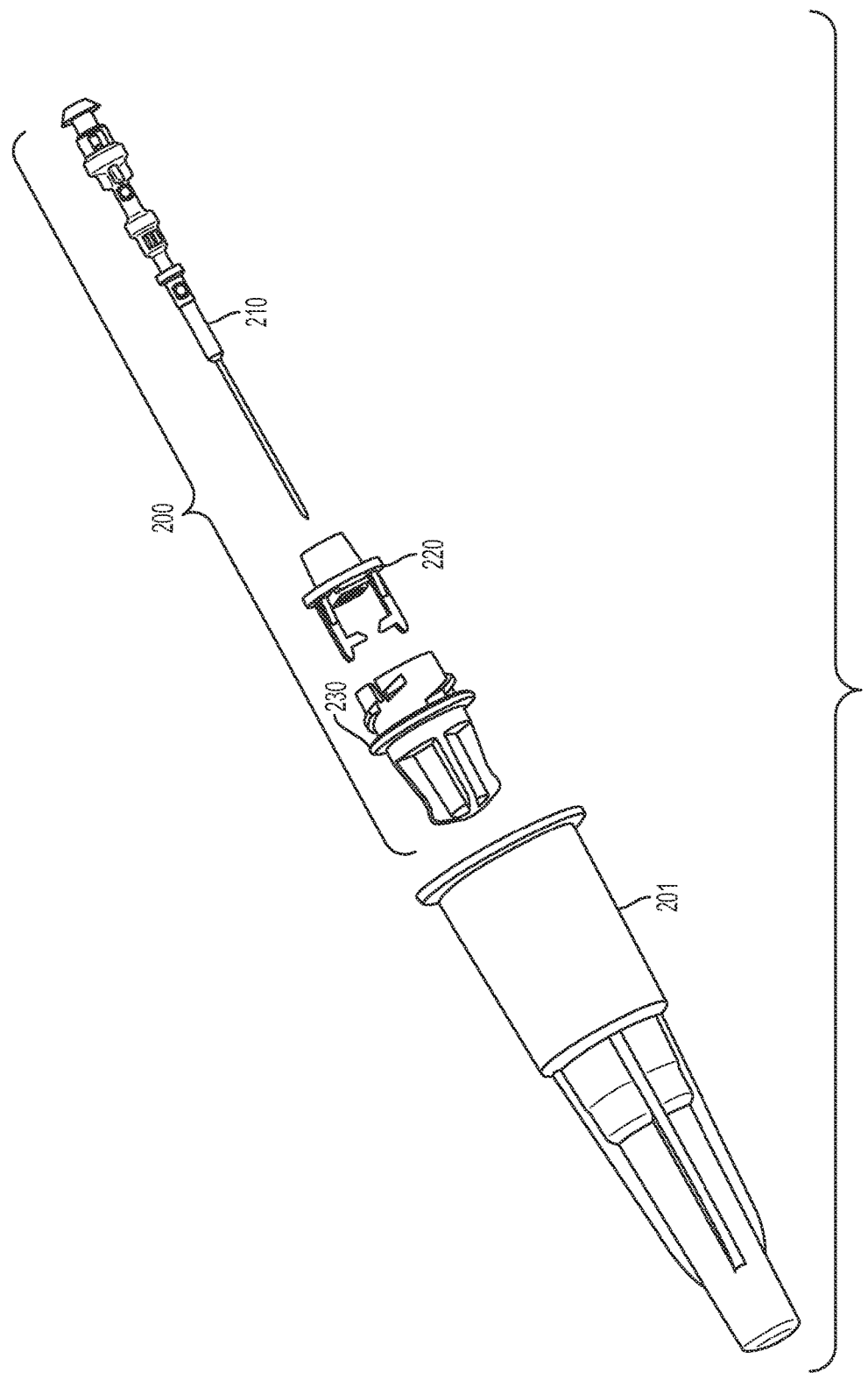
FIG. 5 is an exploded isometric view of a retractable needle assembly and needle cap according to teachings of this disclosure.

Turning now to FIG. 5, the retractable needle assembly 200 is illustrated in exploded form. The retractable needle assembly 200 includes a retractable needle 210, a retainer 220 and a needle hub 230. The retractable needle 210 is received within the needle retainer 220 and the needle hub 230, the needle retainer 220 likewise being at least partially received within the needle hub 230.

Figure 6A:
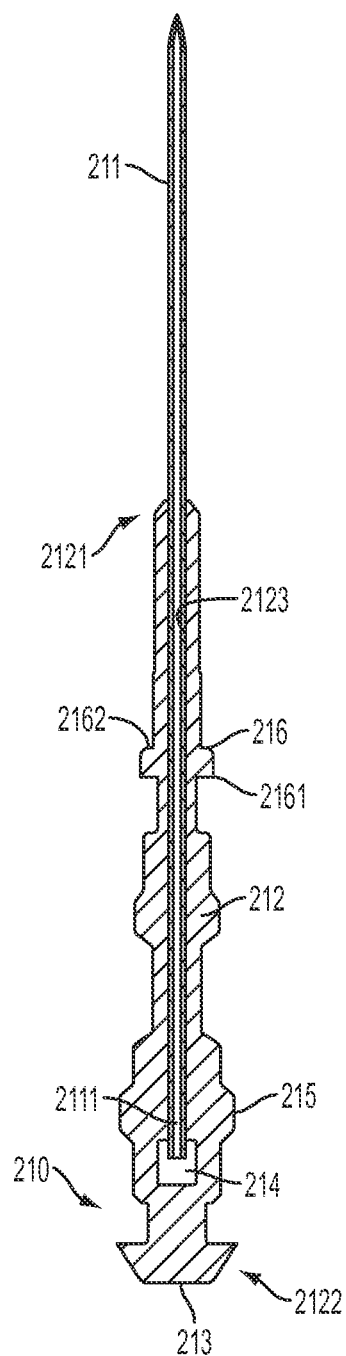
FIG. 6A is a partially cross-sectioned view of a retractable needle and needle-over-mold according to teachings of this disclosure.
Figure 6B:
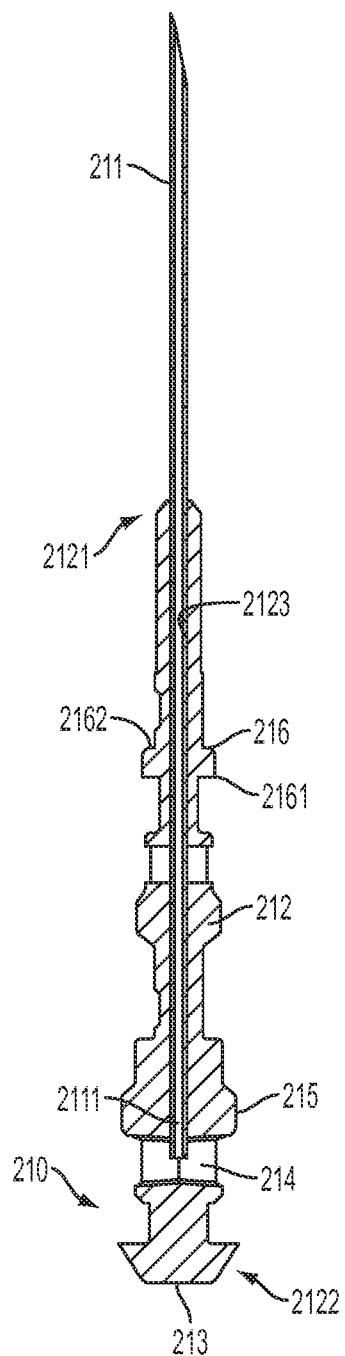
FIG. 6B is a partially cross-sectioned view of the retractable needle and needle-over-mold of FIG. 6A.

Retractable needle 210 is illustrated in greater detail in FIGS. 6A and 6B, which illustrate cross-sections of the retractable needle 210 taken at 90° from one another. The retractable needle 210 includes a cannula 211 having a hollow interior through which fluid may be passed, and a needle body 212 that supports the cannula 211. The needle body 212 is typically a molded polymeric structure, sometimes referenced as a needle-over-mold, with the cannula 211 disposed within an internal channel 2111. The illustrated retractable needle 210 is generally of a type described in WO 2013/067588. In this embodiment, the needle body 212 is an elongated structure with the cannula 211 extending from its distal end 2121. An aperture or window 214 is spaced from a proximal end 2122 of the needle body 212, extending transversely through needle body 212 relative to a longitudinal axis of cannula 211. The window 214 provides fluid communication between the hollow interior 2111 of the cannula 211 and, when assembled to the barrel 100, the fluid chamber 103 of barrel 100 to permit administration of a medicament. While a proximal end of the cannula 211 is illustrated as extending slightly into the window 214, it will be appreciated that the proximal end of the cannula 211 could alternately be disposed within the internal channel 2123 of the needle body 212 spaced from the window 214, or disposed essentially flush with the window 214, so long as fluid communication is still established with the hollow interior 2111 of the cannula 211 by way of the window 214. Those of skill in the art will appreciate that the window 214 may improve access of fluid contents to the proximal end of the cannula 211, thereby minimizing wastage of fluid contents through failure to enter cannula 211. Further, by locating the proximal end of the cannula 211 in a position distal in syringe 1000 with reduced visibility to a user, the user is less inclined to persist with attempts to remove air bubbles which typically collect at a proximal end of the cannula 211, particularly when such action is unlikely to remove the air bubbles, and, rather, wastes the fluid contents of the syringe 1000.

The needle body 212 additionally includes various structures and surfaces that engage with other structures during assembly and operation. For example, one or more peripheral flanges 216 may be spaced from the distal end of the retractable needle 210, presenting abutment surfaces 2161 and 2162 that engage with the retainer 220 and the needle hub 230, respectively. Similarly, a peripheral sealing surface 215 may be provided adjacent or spaced distally from the window 214 for sealing with the needle seal 300. The needle body 212 additionally presents an enlarged coupling member 213 at its proximal end. The coupling member 213 is sized and positioned such that it may be engaged by a complementary mating portion 431 of the plunger seal 430 following administration of a medicament from the syringe 1000. The mating of the complementary mating portion 431 of the plunger seal 430 with the coupling member 213 of the needle body 212 may be, for example, a snap-lock relationship to enable retraction of the retractable needle 210 with a retraction of the plunger rod 410, as will be described in more detail below.

Figure 7A:
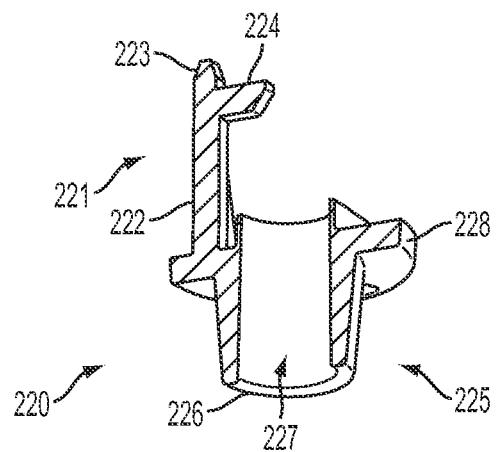
FIG. 7A is a cross-sectional view of a retainer according to teachings of this disclosure.

Referring now to FIG. 7A, there is illustrated an enlarged cross-sectional view of the retainer 220. The retainer 220 generally includes a body 225 having a circumferential shoulder 228 and a neck 226 that presents a passageway 227 through which the retractable needle 210 may be received. In order to removably retain the retractable needle 210 in position within the retractable needle assembly 200, at least one retaining member 221 extends distally from the body 225. The retaining member 221 includes a prong 222, which is cantilevered from the body 225 and includes a distally disposed tip 223. The distally disposed tip 223, along with the circumferential shoulder 228, may be utilized in assembly of the retainer 220 and retractable needle 210 to the needle hub 230. The retaining member 221 additionally presents a lateral projection 224 that is disposed toward the passageway 227 through the retainer 220. In assembly, the lateral projection 224 is disposed subjacent the peripheral flange 216 of the needle body 212 when the retractable needle 210 is assembled into the retainer 220. The lower edge of the lateral projection 224 may be rounded or chamfered to facilitate an axial assembly of the retractable needle 210 through and within the retainer 220. The retaining member 221, including the lateral projections 224, is resilient, and flex to allow the passage of the peripheral flange 216 through the retaining member 221.

Figure 7B:
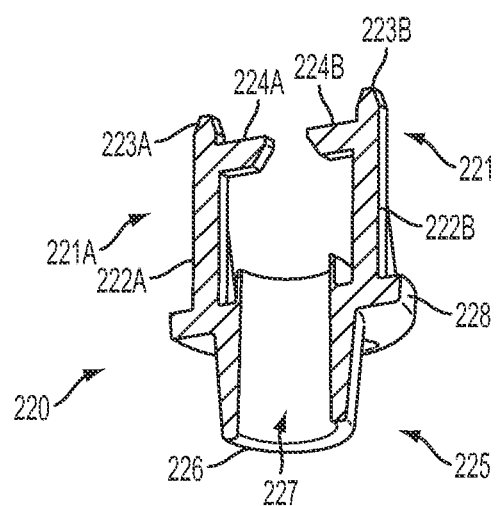
FIG. 7B is a cross-sectional view of an alternate embodiment of a retainer according to teachings of this disclosure.

In the embodiment illustrated in FIG. 7A, a single retaining member 221 is provided. In an alternate embodiment illustrated in FIGS. 5 and 7B, however, a pair of retaining members 221A, 221B is provided. As with the embodiment of FIG. 7A, the retaining members 221A, 221B include prongs 222A, 222B, which are cantilevered from the body 225 and include respective distally disposed tips 223A, 223B. The retaining members 221A, 221B additionally present lateral projections 224A, 224B that are disposed toward the passageway 227 through the retainer 220. In assembly, the lateral projections 224A, 224B are disposed subjacent the peripheral flange 216 of the needle body 212 when the retractable needle 210 is assembled into the retainer 220. One or more of the lower edges of the lateral projections 224A, 224B may be rounded or chamfered to facilitate an axial assembly of the retractable needle 210 through and within the retainer 220. The retaining members 221A, 221B, including the lateral projections 224A, 224B are resilient, and flex to allow the passage of the peripheral flange 216 through the retaining member 221A, 221B.

Those of skill in the art will appreciate that the number, location, and dimensions of the retaining members 221, 221A, 221B are ideally selected based on the forces needed, or needed to be overcome, for retention and retraction, and may also be influenced by, for example, needle length and/or gauge. It will be noted that the same references numbers are utilized with respect to the embodiments of FIGS. 7A and 7B, with the exception of "A" and "B" suffixes where a pair of retaining members is provided. Accordingly, while the references numbers used throughout this disclosure may not include these suffixes, it is to be understood that the reference applies equally to retainers 220 that include one, two, or more retaining members 221.

Figure 8A:
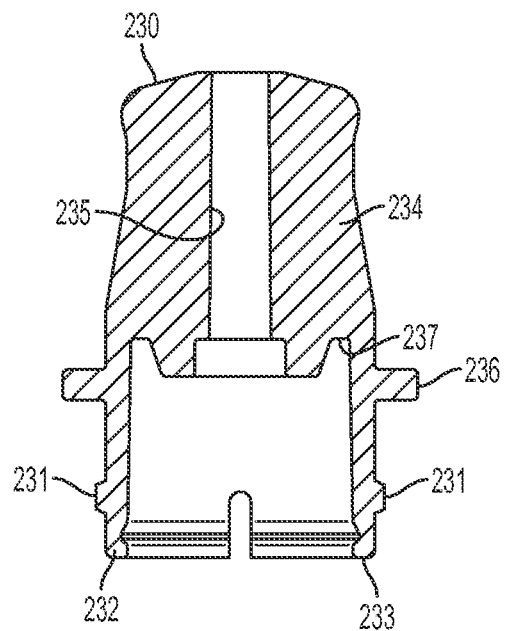
FIG. 8A is a cross-sectional view of a needle hub according to teachings of this disclosure.
Figure 8B:
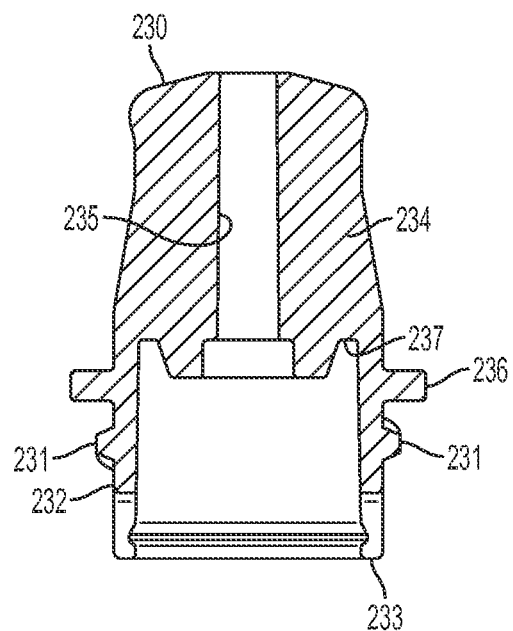
FIG. 8B is a cross-sectional view of the needle hub.

The needle hub 230 is illustrated in FIGS. 8A and 8B, which illustrate cross-sections of the needle hub 230 taken at 90° from one another. The needle hub 230 includes a body 234 from which a skirt 232 depends, the skirt 232 ending in a base 233. An internal channel 235 extending through the body 234 receives the retractable needle 210 in assembly of the retractable needle assembly 200. A peripheral flange 236 extends from at least one of the body 234 or skirt 232 of the needle hub 230, and the body 234 may include a recess 237. The recess 237 may be annularly continuous or discontinuous.

Figure 10A:
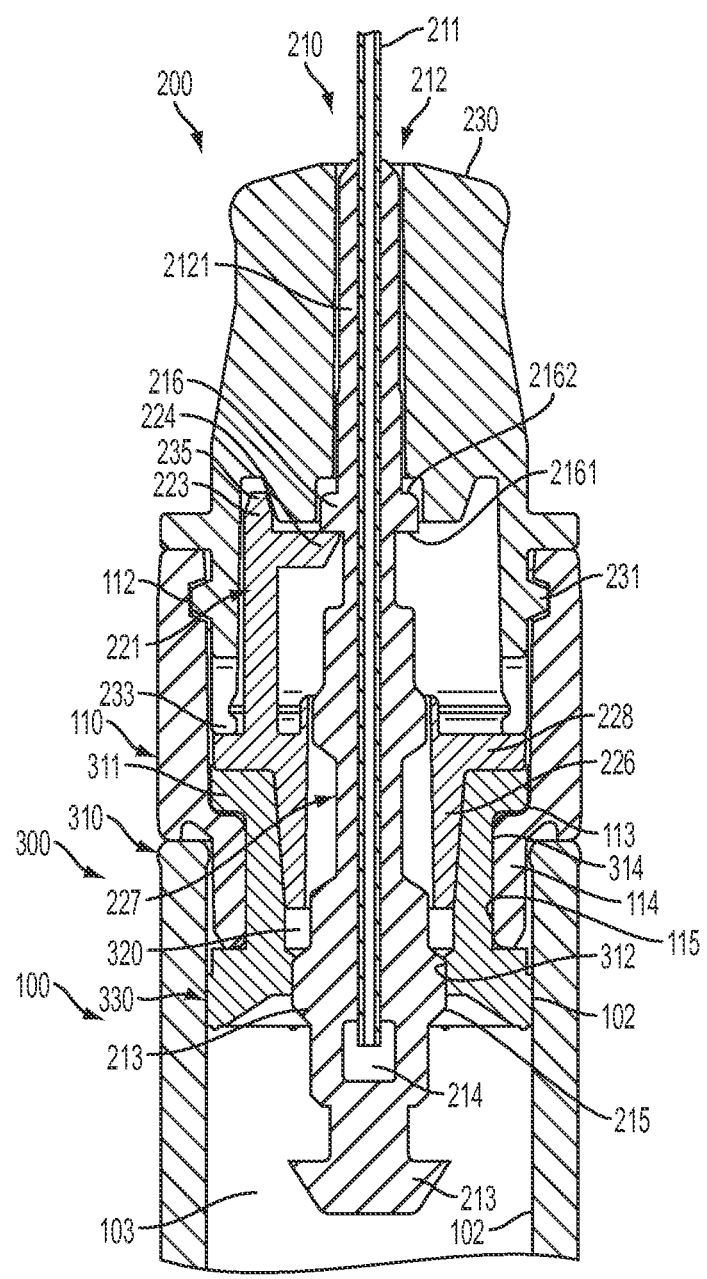
FIG. 10A is a fragmentary, cross-sectional view of an embodiment of a retractable needle assembly coupled to a needle seal in a barrel according to teachings of this disclosure.
Figure 10B:
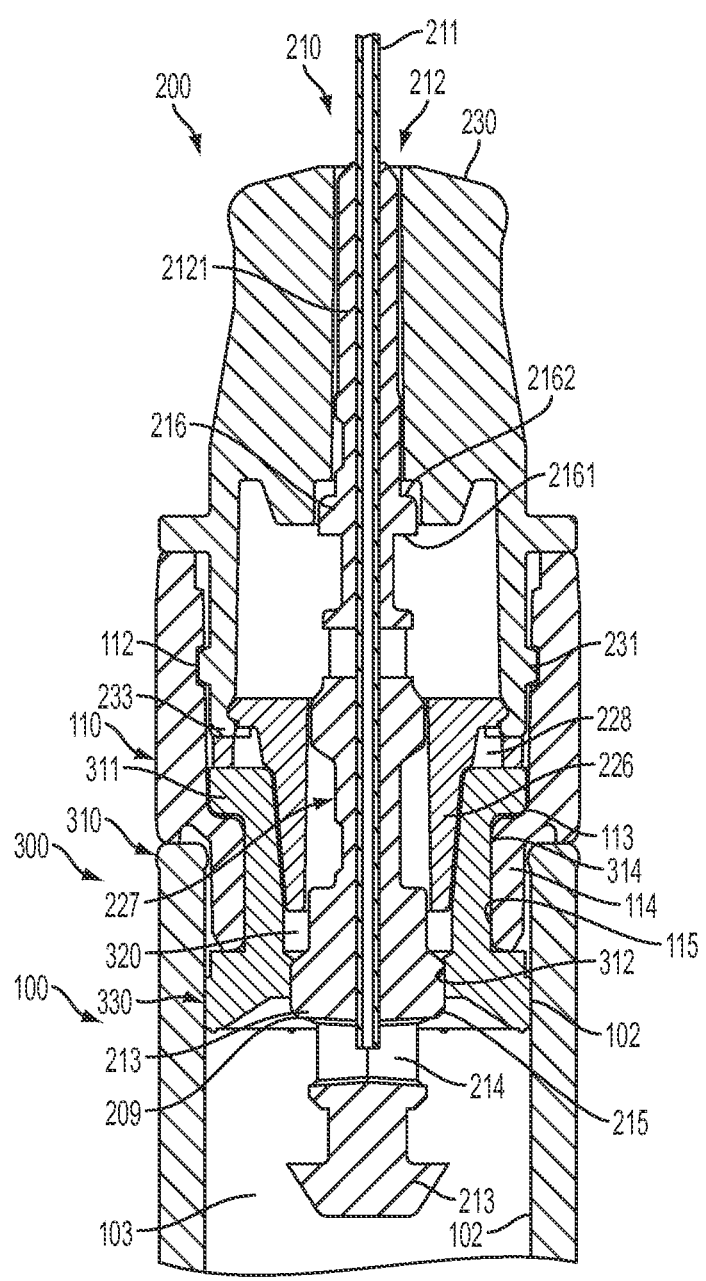
FIG. 10B is a fragmentary, cross-sectional view of the embodiment of FIG. 10A.

Referring again to FIGS. 5 and 9B, in assembly of the retractable needle assembly 200, the retractable needle 210 is inserted into the retainer 220, the retaining member 221 of the retainer 220 flexing to allow the peripheral flange 216 of the retractable needle 210 to pass the lateral projection 224. It will be appreciated that the retaining member 221 is sufficiently resilient to return to substantially their original position with the later projection 224 now subjacent the peripheral flange 216 of the retractable needle 210. The subassembly of the retractable needle 210 and retainer 220 is inserted into the needle hub 230 with a portion of the needle body 212 toward its distal end 2121 being disposed within the internal channel 235 of the needle hub 230, as shown, for example, in FIG. 9B. The retainer 220 is partly housed inside of the needle hub 230. In the assembled state, the distally disposed tip 223 of the retaining member 221 is disposed substantially subjacent the body 234 of the needle hub 230 within a recess 237; the circumferential shoulder 228 of the retainer 220 is disposed subjacent a proximal surface of the skirt 232 of the needle hub 230. When further assembled into the syringe 1000, as illustrated in FIGS. 10A and 10B, the neck 226 of the retainer 220 is housed within the needle seal 300 and the circumferential shoulder 228 of retainer 220 sits between base 233 of needle hub 230 and retaining rim 311 of needle seal 300. It will be appreciated that FIGS. 10A and 10B illustrate cross-sections taken at 90° from one another of the distal end of the syringe 1000 with the attached with retractable needle assembly 200.

The needle hub 230 may be coupled to the mounting member 110 to removably couple the retractable needle assembly 200 to the barrel 100. In the illustrated embodiment, the needle hub 230 further includes coupling structure 231 that is complementary to coupling structure 112 of the mounting member 110. In the illustrated embodiment, the coupling structure 231 of the needle hub 230 is a screw threaded "male" portion that engages a complementary coupling structure 112 in the form of a "female" screw thread on mounting member 110, although the needle hub 230 and the mounting member 110 may be coupled together by any appropriate coupling structure. For example, the retractable needle assembly 200 may be screw-threadedly mounted to barrel wherein the coupling structure 231 of the needle hub 230 may be a "female" screw thread which engages a complementary coupling structure 112 in the form of a "male" screw thread on mounting member 110. Alternately, the coupling structure 231 may include a peripheral rib that engages a coupling structure 112 in the form of a peripheral recess in the mounting member 110 to provide a snap fit.

Figure 13:
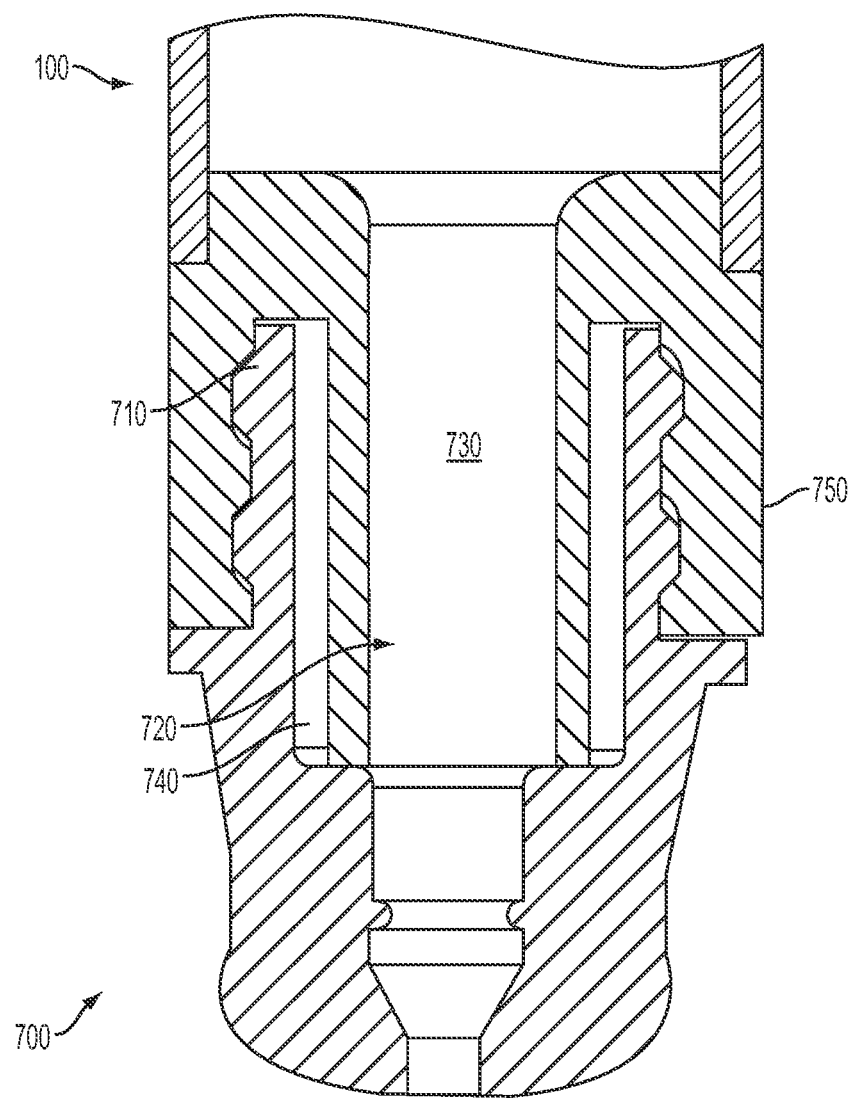
FIG. 13 is a fragmentary, cross-sectional view of an embodiment of conical or tapered, screw-threaded luer adapter according to teachings of this disclosure.

By way of further example, a so-called luer coupling may be provided, as illustrate, for example, in FIG. 13. In this embodiment, luer mount 750 comprises screw thread 710 and conical or tapered male fitment 720, and needle channel 730. Luer adapter 700 is screw-threadedly mounted to a luer mount 750 fitted to a barrel 100, with engagement between the male fitment 720 of the luer mount 750 and a corresponding female fitment 740 of the luer adapter 700, and associated engagement between the corresponding screw-threads 710. The terms "male fitment" and "female fitment" may be used interchangeably to describe corresponding parts and, accordingly, the male or female aspects may be interchanged between the respective components. This configuration may be similar to that known as a luer connection or, more specifically, a luer lock connection.

In assembly of the retractable needle assembly 200 with the syringe 1000, as illustrated in FIGS. 10A and 10B, the enlarged coupling member 213 of the retractable needle 210 is inserted through the needle aperture 320 of the needle seal 300 so that the window 214 of the retractable needle 210 is disposed within the interior of the barrel 100, opening a passageway from the interior of the barrel to the internal channel 2111 of the cannula 211. Further, the peripheral sealing surface 215 of the retractable needle 210 is disposed and seals against the inner sealing rib 312 of the needle aperture 320 of the needle seal 300 to seal the distal end of the fluid chamber 103.

As explained above, when the retractable needle assembly 200 is assembled with the syringe 1000, the retaining member 221 is oriented to project distally with tip 223 being received by recess 237 in needle hub 230. The lateral projection 224 bears against the abutment surface 2161 of abutment 216 in needle body 212 to prevent inadvertent or undesired proximal movement of retractable needle 210. Abutment 216 also bears against needle hub 230, which prevents inadvertent or undesired distal movement of the retractable needle 210. This retaining function can withstand significant force, but nevertheless allow spring-driven retraction of retractable needle 210, as will be described in more detail below.

Returning now to FIG. 9A, in order to maintain a medicament within the barrel 100, a plug 500 may be sealingly disposed in a distal end 101 of the barrel 100, that is, within the distal end of the mounting member 110 prior to attachment of the retractable needle assembly 200. It will be noted that this embodiment of the plug 500 differs somewhat from the embodiment illustrated in FIG. 4. Those of skill in the art will note that the cap or plug 500 of this embodiment includes a nipple 520 that engages and seals the needle aperture 320 of the needle seal 300, retaining the contents and/or interior of the barrel 100 in a sterile environment. As with the coupling of the retractable needle assembly 200, the plug 500 may be removably coupled to the mounting member 110 by any appropriate coupling structure. It will be appreciated, however, that the coupling structure will preferably be the same as or similar to the cooperating structures 231, 112 between the needle hub 230 and the mounting member 110. For example, in the illustrated embodiment, the plug 500 includes a peripheral thread 510 that engages the recessed thread of the mounting member coupling structure 112. As described above with regard to the needle hub 230 and the mounting member 110, an alternate coupling structure, such as a peripheral ridge that engages an internal recess (not shown) may be provided. At the time of use, the cap or plug 500 is decoupled as indicated by the arrow and removed by the user.

According to an aspect of this disclosure, in some uses of the syringe 1000, the barrel 100 may be provided prefilled with fluid contents or with a dehydrated, dried, desiccated, powdered or other reconstitutable solid substance. In embodiments where barrel 100 is prefilled with fluid contents, the cap or plug 500 is removed, as illustrated by the arrow in FIG. 9A, and the retractable needle assembly 200 is then mounted by way of coupling structure 231 of the needle hub 230 engaging complementary coupling structure 112 of the mounting member 110, as illustrated in FIG. 9B and FIGS. 10A and 10B. The air may be cleared, and the fluid contents may be delivered through the cannula 211 once the retractable needle assembly 200 has been coupled to the barrel 100.

In embodiments where barrel 100 of syringe 1000 is provided with a dehydrated, dried, desiccated, powdered or other reconstitutable solid substance, however, the solid substance must be reconstituted by adding fluid to the solid substance. In order to facilitate this reconstitution, the vial adapter 2000 may be utilized in conjunction with the syringe 1000 and a vial 3000 containing the fluid for reconstitution. For the purposes of this explanation, the vial 3000 includes a closure 3100 having a crimped metal cap 3300 that retains a rubber seal 3200 that seals the vial 3000.

Figure 14:
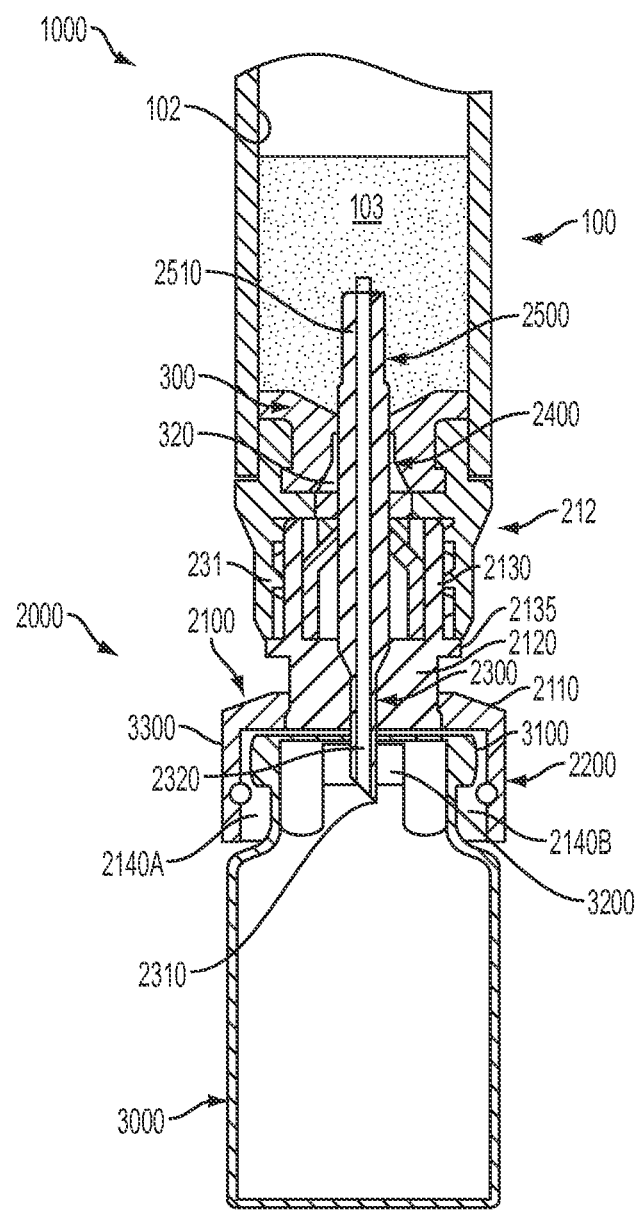
FIG. 14 is a fragmentary, cross-sectional view of a retractable syringe coupled to and in fluid communication with a vial by a vial adapter according to teachings of this disclosure.

An exemplary vial adapter 2000 is illustrated in FIG. 14 in conjunction with the syringe 1000 and a vial 3000. In this embodiment, vial adapter 2000 comprises an adapter housing 2100 having a vial-engaging base 2110, and a syringe-engaging connector 2120.

The vial-engaging base 2110 includes a plurality of flexion arms 2140A, 2140B disposed and adapted to engage the crimped metal cap 3300 of the vial 3000. The flexion arms 2140A, 2140B may be adapted to snap engage any of a variety of different vial closures. The vial-engaging base 2110 is further provided with an adapter cannula 2300. The adapter cannula 2300 projects from the vial-engaging base 2110 of the housing 2100 to provide a sharpened distal tip 2310 adapted to penetrate the rubber seal 3200 of the vial 3000. In order to couple the adapter 2000 to the vial 3000, the vial-engaging base 2110 of the adapter 2000 may be moved into position adjacent the vial 3000. The distal tip 2310 of the adapter cannula 2300 may then be advanced to penetrate the rubber seal 3200 of the vial 3000, the flexion arms 2140A, 2140B surrounding and engaging the vial closure 3100. In order to further protect a user from inadvertent needle-stick injury by distal tip 2310 of adapter cannula 2300, the flexion arms 2140A, 2140B may include a shroud 2200, which extends to substantially surround adapter cannula 2300.

The syringe-engaging connector 2120 includes at least one abutment surface 2130, 2135 adapted to abut one or more surfaces of the mounting member 110 of the syringe 1000. The illustrated embodiment includes a channel structure 2130 that is adapted to be disposed within the mounting member 110, and an abutment flange 2135 adapted to be disposed adjacent a distal surface of the mounting member 110.

The syringe-engaging connector 2120 of the vial adapter 2000 further includes a proximally disposed connector 2400 including conduit tip 2500 that is in fluid communication with adapter cannula 2300 by way of aligned bores 2320 and 2510. After removal of cap or plug 500 from the mounting member 110, the conduit tip 2500 is inserted through into the needle aperture 320 of the needle seal 300 to establish fluid communication between the fluid chamber 103 of the retractable syringe 1000 and vial 3000. In order to provide secure coupling, the abutment surfaces 2130, 2135 are moved into abutment with the mounting member 110. With the vial adapter 2000 in position with the syringe 1000, the inner sealing rib 312 of the needle seal 300 seals against the conduit tip 2500 to provide a sterile fluid connection between the fluid chamber 103 of the syringe 1000 and the vial 3000 by way of the aligned bores 2320, 2510 of the adapter cannula 2300 and the conduit tip 2500. The connector 2400 and conduit 2500 may be sized and disposed that advancing the plunger seal 430 to the connector 2400 and conduit 2500 will not result in the inadvertent actuation of the retraction mechanism, as described below.

It will be appreciated by those of skill in the art that the disclosed vial adapter 2000 may simplify and improve reliability associated with this reconstitution step. The vial adapter 2000 may be maintained in a sterile environment by any suitable arrangement, ensuring the sterility of reconstitution and medication administration. For example, the vial adapter 2000 may be provided with a container similar to the needle cap 201 and cover 202 discussed above.

Following reconstitution, the vial adapter 2000 may be removed from the vial 3000, and the retractable needle assembly 200 positioned on the syringe 1000 for administration of the medicament from the syringe 1000. Thus, the retractable needle assembly 200 may be coupled to the syringe 1000 directly after removal of the cap or plug 500 in the cases of a liquid medicament, or following reconstitution, as, for example, explained with respect to the utilization of the vial adapter 2000. At this point, a user may choose any of a variety of different size or gauge retractable needles, typically provided by way of a kit 90 which may also include the vial adapter 2000 discussed above.

As will be appreciated with further reference to the operation of the plunger below, once the retractable needle assembly 200 is assembled with the syringe 1000, the conduit tip 2500 may prevent inadvertent activation of plunger assembly 400 by preventing depression of plunger assembly 400 to a point where arm 444 is engaged by releasing member 106. If this engagement inadvertently occurs, it would allow plunger rod 410 and plunger housing 420 prematurely disengage to release compressed spring 450.

Figure 11:
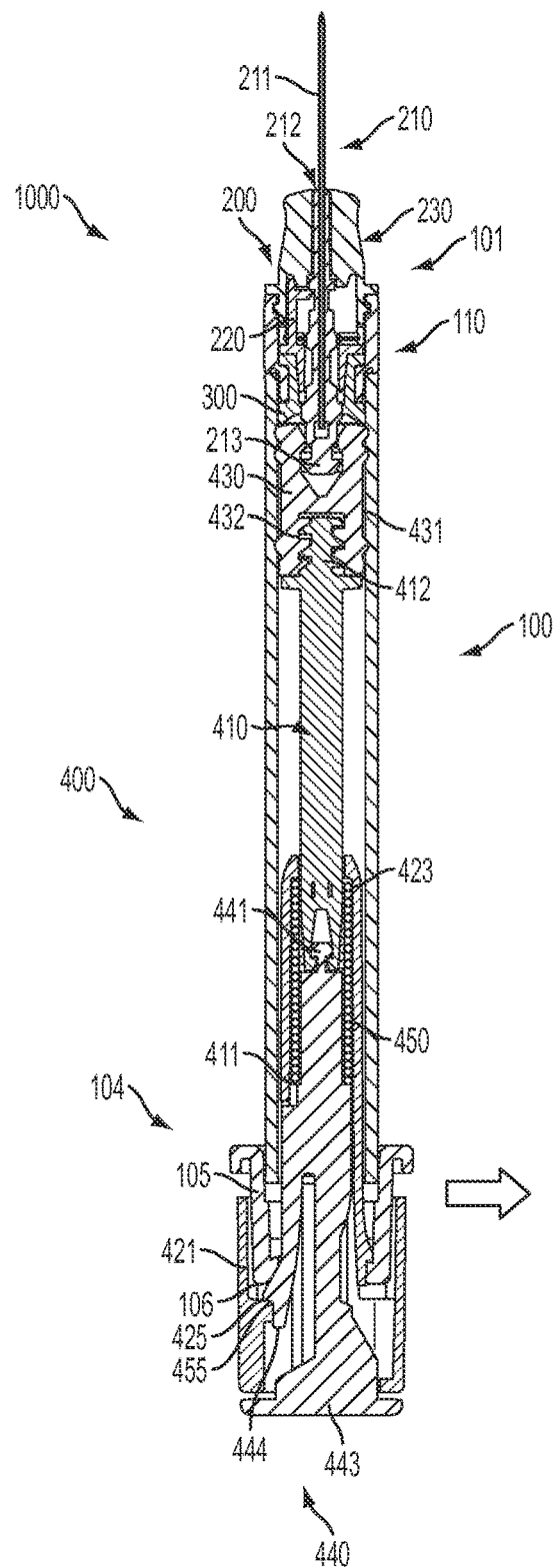
FIG. 11 is a cross-sectional view of the retractable syringe of FIG. 3 after administration and just prior to retraction of a retractable needle.
Figure 12:
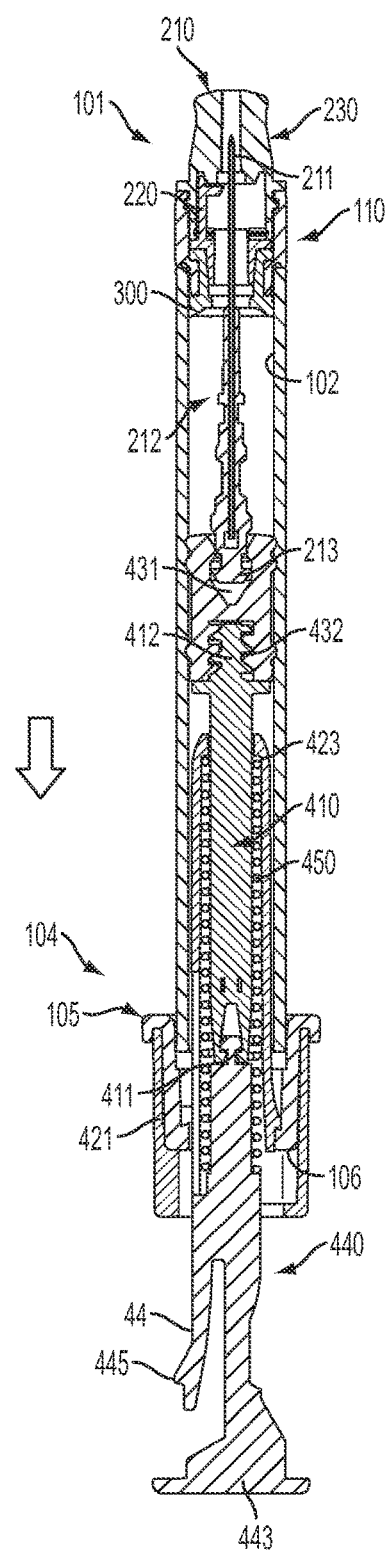
FIG. 12 is a cross-sectional view showing the retractable syringe of FIG. 11 after retraction of the retractable needle.

In order to deliver medication from the syringe 1000, the plunger assembly 400 is adapted to be moved axially towards distal end 101 of barrel 100. The operation of this delivery method is described in greater detail in PCT Application WO2011/057335, which is incorporated herein by reference. At or near the end of plunger assembly 400 depression, complementary mating portion 431 of plunger seal 430 receives and snap-lock engages coupling member 213 of needle body 212. This effectively couples retractable needle 210 to plunger rod 410, as shown in FIG. 11 and FIG. 12. It will also be appreciated that while this embodiment describes male-female engagement between coupling member 213 and complementary mating portion 431, the reverse arrangement is also contemplated.

Following delivery of the medicament, the compressible nature of the plunger seal 430 and needle seal 300 permits continued axial movement of plunger assembly 400. This movement of the plunger housing 420 toward distal end 101 of barrel 100 continues until the release member 106 of the collar 105 bears against and laterally moves the arm 444 of the control rod 440 (in the direction of the arrow), so that the ridge 445 moves out of engagement with the internal tab 425 inside the skirt 421 of the plunger housing 420. This triggers the release of the control rod 440 from the plunger housing 420, allowing the initially compressed spring 450 to expand to deenergize and forcibly bear against annular ledge 411 of the control rod 440, retracting the control rod 440 and the connected plunger rod 410 from the position illustrated in FIG. 11 to the position illustrated in FIG. 12. Retraction of the plunger rod 410 occurs with sufficient force to dislodge the needle body 212 of the retractable needle assembly 200 from the retainer 220 to thereby retract the plunger rod 410, the retractable needle 210 and the control rod 440 releasably connected to the plunger rod 410. The needle seal 300, the needle hub 230 and the retainer 220 remain stationary at the distal end 101 of the barrel 100.

It is noted that dislodgement of the retractable needle 210 from the retainer 220 is substantially axial and involves no twisting, rotation or other torsional force(s) to disengage the needle body 212 from the retainer 220. Furthermore, no "secondary" elements are required, such as an ejector that acts to disengage needle body 212 from retainer 220, thereby providing a more simplified retaining mechanism both in terms of ease and cost of manufacture and also in terms of reliability of operation.

The rate of retraction is controlled by a user relaxing pressure (such as by way of thumb pressure) against the actuation button 443 of the control rod 440. At the end of the plunger assembly 400 depression to complete injection of the fluid contents of the syringe 1000, the plunger housing 420 may be locked to the collar 105 at the proximal end 104 of the barrel 100, to thereby prevent withdrawal of the plunger housing 420 from the barrel 100, as illustrated in FIG. 12, and as described in WO2011/057335. This also facilitates ease of removal of the control rod 440 from the plunger rod 410, disconnecting the releasable connection 441. The releasable connection 441 may be similar to the frangible connection between the control rod and the plunger member, as likewise described in WO2011/057335, or the releasable connection 441 may be a releasable "ball in socket" type connection between the control rod 440 and the plunger rod 410. Once removed from the plunger rod 410, the control rod 440 may then be discarded as "clean" waste, leaving the syringe 1000 with the plunger housing 420 and the plunger rod 410 remaining inside the barrel 100 for a more compact medical waste disposal.

In light of the foregoing it will be appreciated that the present invention provides a relatively simple, robust and inexpensive syringe that is automatically disabled with little or no assistance from the user to thereby prevent, or at least minimize the likelihood of, re-use of the syringe or needle-stick injury to the user. More particularly, the retainer disclosed herein achieves the "balancing act" of providing sufficient retaining function to prevent inadvertent proximal and distal movement of the retractable needle while not preventing spring-driven retraction of the needle at the appropriate time.

Furthermore, the retractable needle assembly allows a user to select a needle of appropriate size of gauge or needle length and/or to replace a needle that becomes bent or burred. Another advantage of the retractable syringe described herein is that it can accommodate and fully encapsulate on retraction, needles of varying length up to 3 inches in length, more preferably up to 1.5 inches (~3.8 cm) in length, thereby providing great flexibility to the user.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A retractable needle assembly for a retractable syringe that includes a plunger assembly and a barrel having a mounting member, said retractable needle assembly comprising:
   a retractable needle engageable by said plunger assembly;
   a needle hub including a proximally projecting skirt, the needle hub mountable to the mounting member of the barrel; and
   a retainer including a body, the body including an outwardly projecting circumferential shoulder, and at least one retaining member that extends distally from the body, the at least one retaining member including an inwardly projecting lateral projection, wherein the outwardly projecting circumferential shoulder is disposed subjacent the proximally projecting skirt and the at least one retaining member is engaged with the retractable needle to prevent inadvertent proximal movement of said retractable needle.

2. The retractable needle assembly of claim 1 wherein the body of retainer further includes an outwardly projecting circumferential shoulder, the at least one retaining member extending from the circumferential shoulder.

3. The retractable needle assembly of claim 1 wherein the retainer further includes a central passageway adapted to receive the retractable needle.

4. The retractable needle assembly of claim 1 wherein each retaining member includes at least one prong having at least one tip and at least one lateral projection.

5. The retractable needle assembly of claim 4 wherein the at least one tip and/or at least one lateral projection are adapted to engage with at least one of the needle hub and the retractable needle.

6. The retractable needle assembly of claim 4 wherein the needle hub includes at least one recess, the at least one tip being disposed within the at least one recess.

7. The retractable needle assembly of claim 1 wherein the needle hub includes a luer mount.

8. The retractable needle assembly of claim 7 wherein the luer mount comprises a conical or tapered luer.

9. The retractable needle assembly of claim 1 wherein the retractable needle is at least partially disposed within the retainer and the needle hub, and the retainer is at least partially disposed within the needle hub.

10. The retractable needle assembly of claim 9 wherein the proximally projecting skirt has a peripheral surface that is threaded.

11. The retractable needle assembly of claim 1 wherein a proximal end of the retractable needle includes a coupling member complimentary to a plunger seal of the plunger assembly.

12. A retractable syringe comprising a retractable needle assembly according to claim 1, a plunger assembly, and a barrel having a mounting member at a distal end, the plunger assembly being disposed at least partially disposed within the barrel and being actuable from a proximal end of the barrel, the retractable needle assembly being coupled to the mounting member.

13. The retractable syringe of claim 12 wherein the needle hub and the mounting member include complementary mounting structures.

14. The retractable syringe of claim 12 wherein the body of the retainer includes an outwardly projecting circumferential shoulder, and the needle hub includes a proximally projecting skirt, the outwardly projecting circumferential shoulder being disposed between the proximally projecting skirt and a distal end of the mounting member.

15. The retractable syringe of claim 12 wherein the plunger assembly includes a plunger seal, an actuating button actuable from a proximal end of the barrel, and a energized biasing element, the plunger seal and a proximal end of the retractable needle including complimentary coupling structures whereby the retractable needle is engaged by the plunger seal when the actuating button is depressed, and the retractable needle is retracted when the biasing element is deenergized.

16. A retractable syringe kit comprising a barrel, a plunger assembly and a plurality of retractable needle assemblies of claim 1.

17. The retractable syringe kit of claim 16, which further including a vial adapter.

18. The retractable syringe kit of claim 17, wherein the vial adapter includes a housing having a base, an adapter cannula that extends or projects from the base and a connector that is capable of being in fluid communication with fluid contents of a vial and the barrel of said retractable syringe, the adapter housing further includes a shroud to protect a user from inadvertent needle-stick injury by said adapter cannula, said shroud including one or more arms that engage a vial closure.

19. The retractable syringe kit of claim 18 wherein the shroud further includes one or more flexion arms that allow the vial adapter to engage any of a variety of different-sized vial closures.

20. The kit of claim 16, wherein the vial adapter further includes a conduit tip mountable or mounted to the connector in fluid communication with the adapter cannula which conduit tip prevents inadvertent activation of a syringe retraction mechanism during fluid transfer.

* * * * *